United States Patent [19]

Giovanni

[11] 4,336,800
[45] Jun. 29, 1982

[54] INTRAVENOUS METERING DEVICE
[75] Inventor: Giovanni Pastrone, Los Gatos, Calif.
[73] Assignee: Oximetrix, Inc., Mountain View, Calif.
[21] Appl. No.: 174,666
[22] Filed: Aug. 1, 1980
[51] Int. Cl.³ ............................................. A61M 5/00
[52] U.S. Cl. ............................. 128/214 F; 417/435; 128/DIG. 12
[58] Field of Search ............. 128/214 E, 214 F, 214.2, 128/273, DIG. 12; 417/435, 443

[56] References Cited

U.S. PATENT DOCUMENTS

| | | | |
|---|---|---|---|
| 2,812,117 | 11/1957 | Butkus et al. | 222/545 |
| 3,559,644 | 2/1971 | Stoft et al. | 128/214 F |
| 3,620,650 | 11/1971 | Shaw | 417/417 |
| 4,030,495 | 6/1977 | Virag | 128/214 F |
| 4,126,132 | 11/1978 | Portner et al. | 128/214 F |
| 4,130,991 | 12/1978 | Wright | 417/443 |
| 4,140,118 | 2/1979 | Jassawalla | 128/214 F |
| 4,142,524 | 3/1979 | Jassawalla et al. | 128/214 F |
| 4,165,208 | 8/1979 | Lundquist | 417/565 |

*Primary Examiner*—Dalton L. Truluck
*Attorney, Agent, or Firm*—Lyon & Lyon

[57] ABSTRACT

A device for precise metering of liquids for intravenous delivery to a patient and its method of use, the device including a pumping chamber with a reciprocable diaphragm positioned therein such that the cross-sectional area of the liquid flow path through this chamber is approximately equal to the cross-sectional area of the inlet and outlet of the chamber. The device also includes check valves positioned at the pumping chamber inlet and outlet and a gas retention chamber having an upper portion providing for the formation of the gas-liquid interface and a lower portion from which liquid free of gas bubbles may be removed.

9 Claims, 3 Drawing Figures

INTRAVENOUS METERING DEVICE

BACKGROUND OF THE INVENTION

Considerable attention has been directed to intravenous delivery of fluids to patients, such as saline solutions and the like, in the last several years. Initially, such materials were administered to a patient by means of gravity flow from a container containing the liquid to be delivered. A difficulty encountered with such devices was that administration by gravity flow often required that the container for the liquid to be transmitted to the patient had to be positioned at a considerable elevation above the patient. Further, attempts to accurately regulate the flow of such devices proved difficult because of the fact that the pressure causing the flow to be transferred to the patient decreased as the liquid level within the container was reduced during the delivery operation.

It is the object of this invention to provide an improved intravenous metering device. Other and additional objects become apparent upon a reading of the entire specification, drawings and claims.

DRAWINGS

FIGS. 2 and 3 are partial cross-sectional views illustrating the subject matter of this invention.

DESCRIPTION OF PREFERRED EMBODIMENTS

Figure 1:
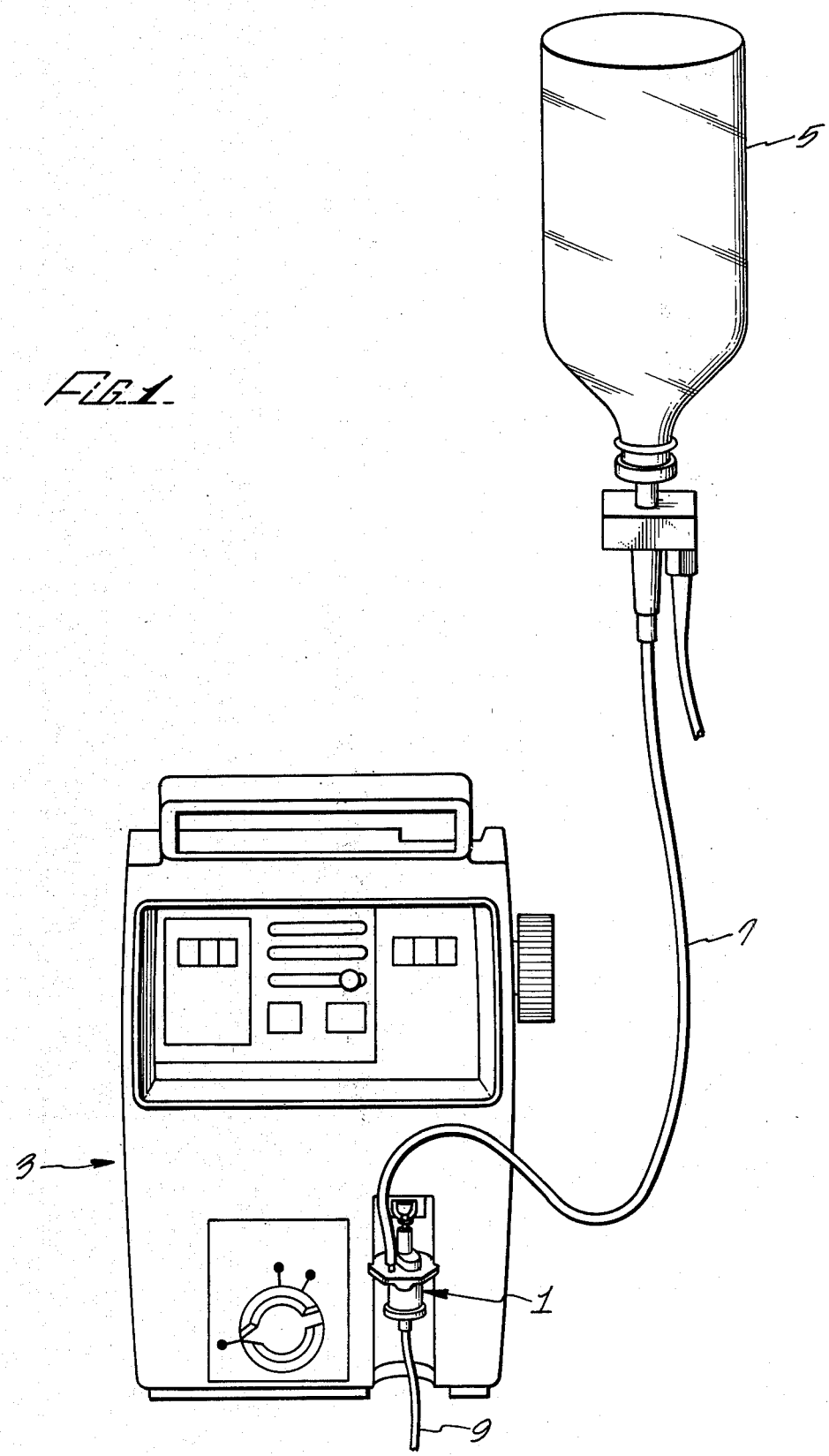
FIG. 1 is a pictorial view illustrating the use of the present invention.

Referring now to FIG. 1, the intravenous metering device 1 is shown positioned within a metering device control unit 3. The intravenous metering device 1 is connected to a container of fluid 5 by means of conventional tubing 7. Tubing 9, extending from the outlet of the intravenous metering device 1 transfers precise amounts of fluid to the patient to be treated.

Figures 2, 3:
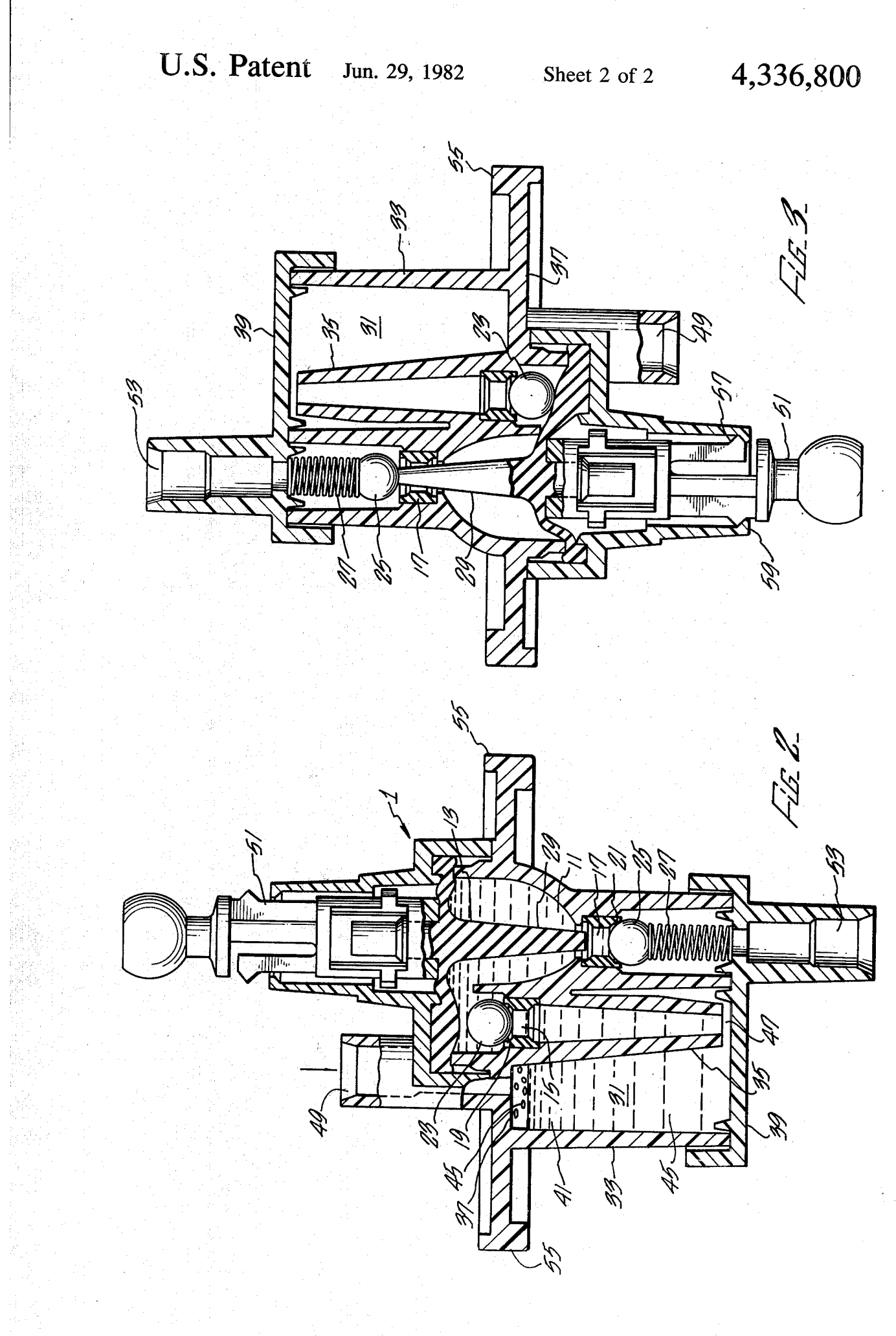

Referring now to FIG. 2, the construction of the intravenous metering device 1 of the present invention will be discussed in detail. The intravenous metering device 1 includes a pumping chamber 11 and a reciprocable diaphragm 13 which is positioned within the pumping chamber 11, and preferably at the approximate center of the pumping chamber 11. The intravenous metering device 1 includes a pumping chamber inlet 15 and a pumping chamber outlet 17. Pumping chamber inlet 15 includes a valve seat means 19. Similarly, pumping chamber outlet 17 includes valve seat means 21. Ball checks 23 and 25 are positioned such that they are normally in a position so as to seat against valves seats 19 and 21 of the pumping chamber inlet 15 and pumping chamber outlet 17, respectively. The ball check 23 is normally held in the closed position by gravity while the ball check 25 is normally held in the closed position by biasing means such as spring 27.

The reciprocable diaphragm 13 includes a projection 29, preferably centered within the pumping chamber 11 such that the cross-sectional area of the liquid flow path through the pumping chamber 11 is approximately equal to the cross-sectional area of the pumping chamber inlet 15 and the pumping chamber outlet 17. One of the advantages of this relationship is the relatively constant, high velocities of fluid flow experienced during the filling operation of the intravenous metering device 1, which will be discussed in greater detail when reference is made to FIG. 3.

The intravenous metering device 1 further includes a gas retention chamber 31 bounded by sidewalls 33 and 35 and gas retention chamber opposed walls 37 and 39. As shown in FIG. 2, the gas retention chamber 31 includes a gas retention chamber upper portion 41 providing for a gas-liquid interface 43, and a gas retention chamber lower portion 45 from whence liquid free of gas bubbles may pass from the gas retention chamber lower portion 45 through a gas retention chamber passageway 47 and into the pumping chamber 11.

The detailed construction of the intravenous metering device 1 of this invention having been described, its method of operation will now be discussed. Incoming fluid, transmitted by tubing such as 7 to the intravenous metering device inlet 49 passes into the gas retention chamber 31 which, due to the extension of side wall 35 prevents any gases therein from entering the pumping chamber 11 and allows for the generation of a gas-liquid interface 43 at the gas retention chamber upper portion 41. Liquid free of gas bubbles passes from the gas retention chamber lower portion 45 through gas retention chamber passageway 47. When the intravenous metering device shaft 51 is reciprocated upwardly, the volume of the pumping chamber 11 is increased by a precise and predetermined amount and the pressure within the pumping chamber 11 correspondingly decreased. This pressure decrease within the pumping chamber 11 is sufficient to lift pumping chamber inlet ball check 23 from pumping chamber inlet valve seat 19 so as to allow the liquid free of gas bubbles to enter the pumping chamber 11. As the reciprocable diaphragm 13 is reciprocated downwardly by means of the intravenous metering device shaft 51, the volume within the pumping chamber 11 is decreased and the pressure within the pumping chamber 11 increased. This increase in pressure within the pumping chamber 11 causes pumping chamber chamber inlet ball check 23 to seat against pumping chamber inlet valve seat 19 thus preventing fluid flow from the pumping chamber 11 to the gas retention chamber 31. Simultaneously, the increase in pressure within pumping chamber 11 overcomes the biasing means 27 urging pumping chamber outlet ball check 25 to engage pumping chamber outlet valve seat 21 thereby allowing a precise amount of metered fluid to be pumped from the pumping chamber 11 through the intravenous metering device outlet 53 to a patient as by means of tubing 9. The intravenous metering device 1 includes shoulders 55 for the positioning of the intravenous metering device 1 within the metering device control unit 3 that provides control for the reciprocation of the intravenous metering device shaft 51 and the reciprocable diaphragm 13 attached thereto.

FIG. 3 illustrates the orientation and configuration of the intravenous metering device 1 when it is to be filled with liquid to be administered to a patient and placed in service. The intravenous metering device of the present invention may be disposable such that a fresh and sterilized intravenous metering device 1 is employed at each application of intravenous passage of fluid to a patient. As illustrated in FIG. 3, the intravenous metering device 1 is rotated 180 degrees in order to be filled with liquid. During this filling operation, the intravenous metering device shaft 51 is manually depressed beyond its normal travel length such that intravenous metering device shaft detent 57 is engaged by a corresponding shoulder 59 of the intravenous metering device 1. The projection 29 of the reciprocable diaphragm 13 is constructed such that it may pass through the pumping chamber outlet 17 and overcome the biasing means 27 acting upon the pumping chamber outlet ball check 25 thereby allowing fluid to flow through the intravenous metering device outlet 53 and the pumping chamber outlet 17 from the pumping chamber 11. Because the pumping chamber inlet ball check 23 is normally positioned in the closed position as shown in FIG. 2 by force of gravity, rotation of the intravenous metering device 1 as shown in FIG. 3 also opens the pumping chamber inlet 15 thereby allowing the flow of liquid to pass into the pumping chamber 11 from the gas retention chamber 31 and the intravenous metering device inlet 49. The configuration of the reciprocable diaphragm 13 and its projection 29 is such that when depressed as shown in FIG. 3, the cross-sectional area of the liquid flow path through chamber 11 is approximately equal to the cross-sectional area of the pumping chamber inlet 15 and the pumping chamber outlet 17. Accordingly, during the filling operation as illustrated in FIG. 3, the fluid fills the intravenous metering device at a substantially constant velocity thereby sweeping out gases present in the intravenous metering device for use. Further, the orientation of the reciprocable diaphragm 13 at the approximate center of the pumping chamber 11 produces a swirling liquid flow path about the reciprocable diaphragm projection 29 as the liquid enters the intravenous metering device thereby creating a swirling fluid flow and sweeping out gases present within the intravenous metering device 1 prior to usage of the device. It is of critical importance that such gases be removed from the pumping chamber in order to ensure that precise amounts of fluid are administered to a patient. In the event that gases are present within the pumping chamber 11, the gases, being compressible as contrasted with a liquid, will alter the amount of liquid transferred to the patient during each reciprocation of the reciprocable diaphragm 13. The presence of gases within the pumping chamber 11 is effectively foreclosed by the configuration of the device allowing for the filling with a swirling liquid action at constant high velocity as shown in FIG. 3 and the employment of the gas retention chamber 31 during normal operation of the device as was more particularly described in the explanation of FIG. 2 of the drawings.

It is obvious that certain changes can be made to the preferred form of the invention as described above. Accordingly, the claims should be given an interpretation commensurate with the scope of the invention as set out in the claims appended hereto.

What is claimed is:

1. A device which precisely meters fluids for intravenous delivery from a source of fluid to a patient, said device comprising:

a fluid pumping means for receiving fluid and for metering fluid so received to the patient, said fluid pumping means including a pumping chamber together with means for varying the volume of said pumping chamber;

an inlet means for permitting fluid to enter said fluid pumping means, said inlet means including a pumping chamber inlet in fluid communication with said pumping chamber, said inlet means also including a first valve means positioned within said pumping chamber inlet to control the entry of fluid into said fluid pumping means;

an outlet means for permitting fluid to exit said fluid pumping means, said outlet means including a pumping chamber outlet in fluid communication with said pumping chamber, said outlet means also including a second valve means positioned within said pumping chamber outlet to control the exit of fluid from said fluid pumping means;

a support structure having a device inlet formed therein for connection to the source of fluid; and gas retention chamber means interposed between said support structure and said inlet means for providing a circuitous fluid path from said device inlet to said pumping chamber inlet such that fluid received by said fluid pumping means is free of gas bubbles, said gas retention chamber means including an upper chamber portion having a shape which enables the formation of a gas-liquid interface therein, said gas retention chamber means also including a lower chamber portion disposed below said pumping chamber inlet for holding liquid free of gas bubbles and a passageway means lower chamber portion disposed below said pumping chamber inlet for holding liquid free of gas bubbles and a passageway means connected between said lower chamber portion and said inlet means for passing liquid free of gas bubbles in an upward direction from said lower chamber portion to said pumping chamber inlet.

2. A device as set forth in claim 1, wherein said passageway means includes a structural wall member having a passageway disposed therein, said passageway extending downward from said pumping chamber inlet to said lower chamber portion to provide for the passage of fluid therebetween.

3. A device as set forth in claim 1, wherein said means for varying the volume of said pumping chamber includes a diaphragm means positioned within said pumping chamber for reciprocable movement in upward and downward directions such that the pressure inside said pumping chamber decreases as said diaphragm means moves in said upward direction while the pressure inside said pumping chamber decreases as said diaphragm means moves in said downward direction.

4. A device as set forth in claim 3, wherein said diaphragm means includes a projection extending into said pumping chamber.

5. A device as set forth in claim 4, including a shaft means secured to said diaphragm means for reciprocation thereof, said shaft means including a detent for locking said shaft means in a position such that said projection of said diaphragm means forces said second valve means into an open position.

6. A device as set forth in claim 1, wherein said first valve means includes a first valve element normally biased by gravity to a closed position but movable to an open position for the purpose of permitting fluid free of gas bubbles to enter said fluid pumping means from said lower portion of said gas retention chamber means in response to an increase in the volume of said pumping chamber.

7. A device as set forth in claim 6, wherein said first valve element is a ball check.

8. A device as set forth in claim 6, wherein said second valve means includes a second valve element normally biased to a closed position by a biasing member but movable to an open position to permit the exit of fluid from said pumping chamber through said pumping chamber outlet in response to a decrease in the volume of said pumping chamber.

9. A device as set forth in claim 8, wherein said second valve element is a ball check and said biasing member is a spring.

* * * * *